US00PP11806P2

(12) United States Plant Patent
Underhill, Jr.

(10) Patent No.: US PP11,806 P2
(45) Date of Patent: Mar. 13, 2001

(54) LEATHERLEAF FERN PLANT NAMED 'UNDERHILL'

(75) Inventor: Frank Elmore Underhill, Jr., DeLand, FL (US)

(73) Assignee: Underhill Ferneries, Barberville, FL (US)

( * ) Notice: Subject to any disclaimer, the term of this patent is extended or adjusted under 35 U.S.C. 154(b) by 0 days.

(21) Appl. No.: 09/334,022

(22) Filed: Jun. 15, 1999

(51) Int. Cl.[7] ..... A01H 5/00
(52) U.S. Cl. ..... Plt./379

(58) Field of Search ..... Plt./379

*Primary Examiner*—Bruce R. Campell
*Assistant Examiner*—Melissa L. Kimball
(74) *Attorney, Agent, or Firm*—C. A. Whealy

(57) ABSTRACT

A distinct cultivar of Leatherleaf Fern plant named 'Underhill', characterized by its upright and outwardly arching plant habit; moderate vigor and rapid growth rate; dark burgundy-colored rachis that are durable and strong; numerous pinnules per frond that are medium green, glossy, with finely and deeply serrate margins and acute apices which give a fringed lacy appearance to the frond; overlapping pinnules which give a full and dense appearance to the frond; and no spores.

2 Drawing Sheets

BACKGROUND OF THE INVENTION

The present invention relates to a new and distinct cultivar of Leatherleaf Fern plant, botanically known as *Rumohra adiantiformis*, and hereinafter referred to by the cultivar name Underhill.

The new cultivar was discovered by the Invention in Barberville, Fla., as a naturally-occurring mutation within a cultivated population of the *Rumohra adiantiformis* cultivar Mayfield, not patented.

Since September, 1994, asexual reproduction by division and by tissue culture of the new Leatherleaf Fern at Barberville, Fla., has shown that the unique features of this new Leatherleaf Fern are stable and retained through at least eight successive generations of asexual reproduction.

SUMMARY OF THE INVENTION

The new Leatherleaf Fern has not been observed under all possible environmental conditions. The phenotype may vary somewhat with variations in environment such as temperature, light intensity and fertilizer regime, without, however, any variance in genotype. The following observations, measurements and comparisons describe plants grown in Barberville, Fla., under conditions generally used in commercial Leatherleaf Fern production.

The following traits have been repeatedly observed and are determined to be the unique characteristics of Underhill. These characteristics in combination distinguish Underhill as a new and distinct cultivar:

1. Upright and outwardly arching plant habit.

2. Moderate vigor and rapid growth rate.

3. Dark burgundy-colored rachis that are durable and strong; fronds resist breakage during transport.

4. Numerous pinnules per frond that are medium green, glossy, with finely and deeply serrate margins and acute apices gives a fringed lacy appearance to the frond.

5. Overlapping pinnules gives a full and dense appearance to the frond.

6. No spore formation.

The new Leatherleaf Fern can be compared to its parent cultivar, the cultivar Mayfield. However in side-by-side comparisons conducted in Barberville, Fla., plants of the new Leatherleaf Fern differ from plants of the cultivar Mayfield in the following characteristics:

1. Plants of the new Leatherleaf Fern develop larger and thicker rhizomes than plants of the cultivar Mayfield.

2. Rachis are shorter, stronger and more durable on plants of the new Leatherleaf Fern than rachis of plants of the cultivar Mayfield. In addition, rachis of plants of the new Leatherleaf Fern are burgundy in color whereas rachis of plants of the cultivar Mayfield are mostly green and brown at the base.

3. Plants of the new Leatherleaf Fern have broader fronds than plants of the cultivar Mayfield.

4. Pinnules of plants of the new Leatherleaf Fern are thinner, more deeply serrate and appear finer and lacier than pinnules of plants of the cultivar Mayfield.

5. Pinnules of plants of the new Leatherleaf Fern overlap more than pinnules of plants of the cultivar Mayfield which give a more densely foliated and fuller appearance to the new Leatherleaf Fern.

6. Pinnules of plants of the new Leatherleaf Fern are lighter green in color than pinnules of plants of the cultivar Mayfield.

7. Plants of the new Leatherleaf Fern have not been observed to develop spores whereas plants of the cultivar Mayfield typically develop spores.

The new Leatherleaf Fern can be compared to the *Rumohra adiantiformis* cultivar Newbold's Diamond, disclosed in U.S. Plant Pat. No. 9,113 and U.S. Pat. No. 5,650,551. However in side-by-side comparisons conducted in Barberville, Fla., plants of the new Leatherleaf Fern differ from plants of the cultivar Newbold's Diamond in the following characteristics:

1. Pinnules of plants of the new Leatherleaf Fern are more deeply serrate and appear finer and lacier than pinnules of plants of the cultivar Newbold's Diamond.

2. Pinnules of plants of the new Leatherleaf Fern overlap more than pinnules of plants of the cultivar Newbold's Diamond which give a more densely foliated and fuller appearance to the new Leatherleaf Fern.

3. Pinnules of plants of the new Leatherleaf Fern are lighter green in color than pinnules of plants of the cultivar Newbold's Diamond.

4. Plants of the new Leatherleaf Fern have not been observed to develop spores whereas plants of the cultivar Newbold's Diamond typically develop spores.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a top perspective view of a typical frond of 'Underhill'.

The photograph at the top of the second sheet comprises a top perspective view of typical fronds of 'Mayfield' (left) and 'Underhill' (right).

The photograph at the bottom of the second sheet comprises a close-up view of typical pinnules of 'Mayfield' (left) and 'Underhill' (right). Pinnules and rachis colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. Measurements and numerical values represent averages for typical fronds from three-year old plants produced by division grown in ground beds under a polypropylene-covered shade house that provided a 73 percent light reduction with day temperatures about 27° C. and night temperatures about 18° C.

Botanical classification: *Rumohra adiantiformis* cultivar Underhill.

Commercial classification: Cut foliage plant.

Parentage: Naturally-occurring mutation of the *Rumohra adiantiformis* cultivar Mayfield, not patented.

Propagation: By division and by tissue culture.

Root description: Root system fibrous with thick rhizomes.

Plant description:

*Plant shape/growth habit.*—Individual fronds are upright and outwardly arching; numerous fronds per plant. Open plant habit.

*Height.*—32 cm.

*Width.*—42 cm.

*Plant vigor.*—Moderately vigorous.

*Growth rate.*—Rapid.

*Frond description.*—Shape: Triangular. Leaf arrangement: Three-pinnate. Length: About 32 cm. Width: About 41 cm.

*Rachis description.*—Length: About 63 cm. Diameter: About 5 mm. Strength: Strong and durable; resists breakage during transport. Color: Immature: Green, 146A. Mature: Burgundy, close to 187B, to very dark burgundy, 187A, to darker than 187A.

*Pinnae/pinnule description.*—Pinnule shape: Roughly ovate. Quantity: Primary pinnae per rachis: About 17. Secondary pinnae per primary pinnae: About 17. Pinnules per secondary pinnae: About 17. Length: Primary pinnae: About 32 cm. Secondary pinnae: About 14.2 cm. Pinnules: About 6.5 cm. Width: Primary pinnae: About 41 cm. Secondary pinnae: About 11.4 cm. Pinnules: About 3.2 cm. Pinnule margin: Finely and deeply serrated; lacy appearance. Pinnule apex: Acute, pointed. Pinnule base: Attenuate. Pinnule aspect: Flat to somewhat concave. Pinnule attachment: Petiolate. Petiole length: About 3 mm. Pinnule texture: Glabrous, glossy. Pinnule color: Immature, upper surface: Greener than 146A. Immature, lower surface: Greener than 146A. Mature, upper surface: Greener than 147A, glossy. Mature, lower surface: 147B. Pinnule venation pattern: Pinnate.

*Spores.*—None observed.

Disease resistance: Resistance to diseases common to Leatherleaf Ferns has not been observed.

It is claimed:

1. A new and distinct cultivar of Leatherleaf Fern plant named 'Underhill', as illustrated and described.

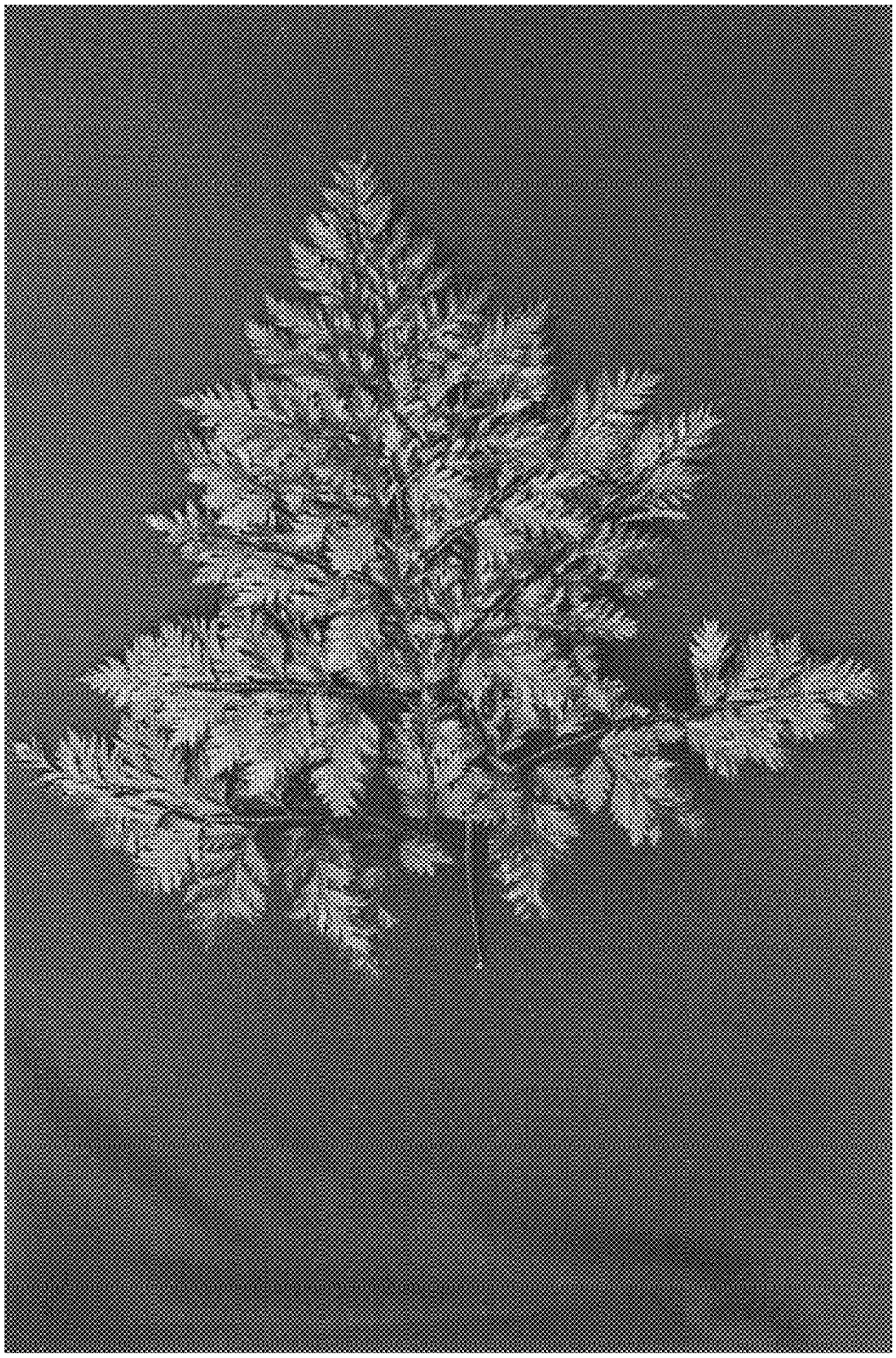

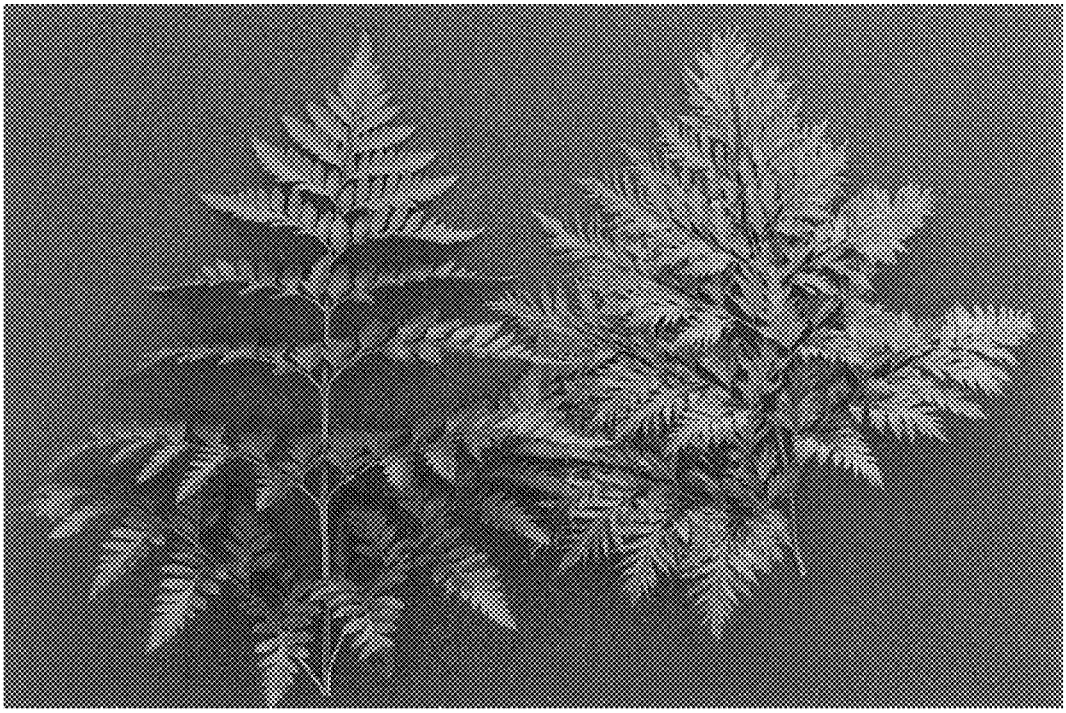
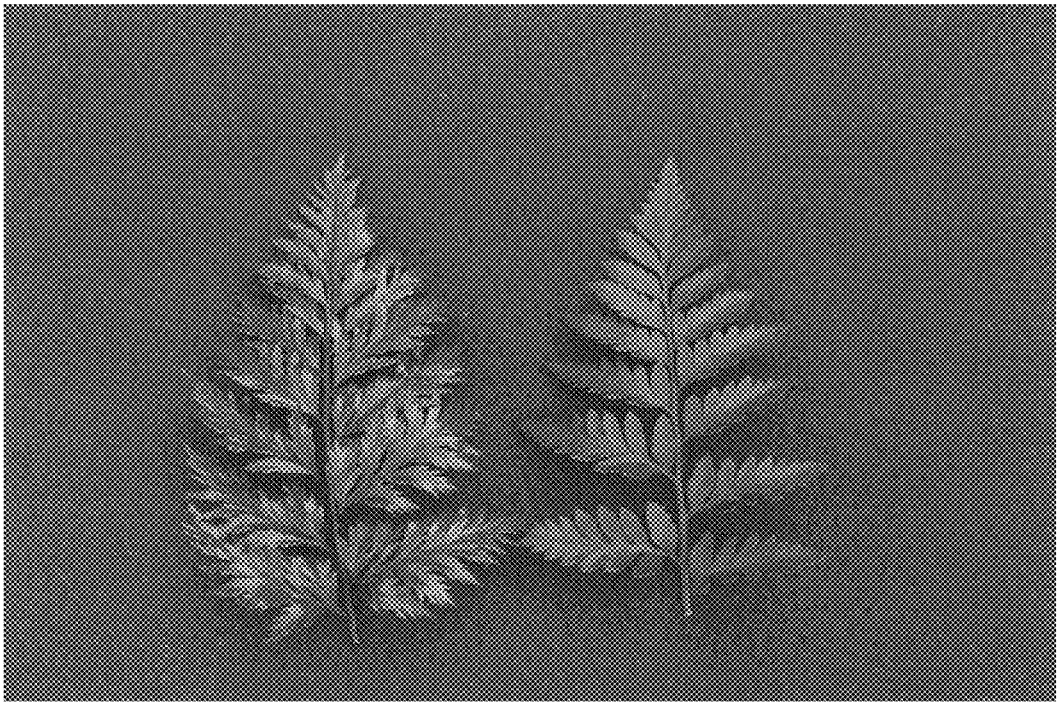

* * * * *